(12) United States Patent
Nanba et al.

(10) Patent No.: US 11,015,159 B2
(45) Date of Patent: May 25, 2021

(54) SINGLE-USE CELL CULTURING APPARATUS AND CULTURING BAG

(71) Applicants: HITACHI, LTD., Tokyo (JP); FUJIMORI KOGYO CO., LTD., Tokyo (JP)

(72) Inventors: Masaru Nanba, Tokyo (JP); Takashi Andou, Tokyo (JP); Yui Sugita, Tokyo (JP); Sei Murakami, Tokyo (JP); Hiroyuki Matsuda, Tokyo (JP)

(73) Assignees: HITACHI, LTD., Tokyo (JP); FUJIMORI KOGYO CO., LTD., Tokyo (JP)

( * ) Notice: Subject to any disclaimer, the term of this patent is extended or adjusted under 35 U.S.C. 154(b) by 0 days.

(21) Appl. No.: 15/749,609

(22) PCT Filed: Jul. 1, 2016

(86) PCT No.: PCT/JP2016/069631
§ 371 (c)(1),
(2) Date: Feb. 1, 2018

(87) PCT Pub. No.: WO2017/026199
PCT Pub. Date: Feb. 16, 2017

(65) Prior Publication Data
US 2018/0223233 A1 Aug. 9, 2018

(30) Foreign Application Priority Data
Aug. 7, 2015 (JP) .............................. JP2015-157084

(51) Int. Cl.
*C12M 1/06* (2006.01)
*C12M 3/00* (2006.01)
(Continued)

(52) U.S. Cl.
CPC .............. *C12M 1/06* (2013.01); *C12M 1/007* (2013.01); *C12M 1/02* (2013.01); *C12M 3/00* (2013.01);
(Continued)

(58) Field of Classification Search
CPC .......... C12M 1/06; C12M 1/007; C12M 1/02; C12M 3/00; C12M 23/14; C12M 23/26; C12M 23/48; C12M 27/20
See application file for complete search history.

(56) References Cited

U.S. PATENT DOCUMENTS 1,873,523 A * 8/1932 Abbott .................... E05G 1/024
109/83
4,665,035 A 5/1987 Tunac
(Continued)

FOREIGN PATENT DOCUMENTS

CN 1578830 A 2/2005
EP 1 451 290 B1 1/2011
(Continued)

OTHER PUBLICATIONS

International Search Report of PCT/JP2016/069631 dated Sep. 6, 2016.
(Continued)

*Primary Examiner* — William H. Beisner
*Assistant Examiner* — Danielle B Henkel
(74) *Attorney, Agent, or Firm* — Mattingly & Malur, PC

(57) ABSTRACT

A single-use cell culturing apparatus and a culturing bag are provided, each of which can improve efficiency of stirring a culture solution and further reduce a possibility of leakage of the culture solution. The single-use cell culturing apparatus of the present invention includes a housing that accommodates the culturing bag which is flexible and can seal the culture solution inside thereof. The housing has, on an inner (Continued)

surface thereof, a curved convex-shaped protrusion provided at a portion of a contact face at which the housing is in contact with the culturing bag. The culturing bag of the present invention is accommodated in the housing of the single-use cell culturing apparatus; is flexible; and can seal the culture solution inside thereof. The culturing bag includes a concave portion having a shape corresponding to the curved convex protrusion disposed on a part of the housing.

11 Claims, 9 Drawing Sheets

(51) Int. Cl.
 *C12M 1/00* (2006.01)
 *C12M 1/02* (2006.01)
(52) U.S. Cl.
 CPC ............ *C12M 23/14* (2013.01); *C12M 23/26* (2013.01); *C12M 23/48* (2013.01); *C12M 27/20* (2013.01)

(56) References Cited

U.S. PATENT DOCUMENTS

| | | | | |
|---|---|---|---|---|
| 5,558,437 | A * | 9/1996 | Rode | B01F 11/0014 366/208 |
| 7,645,065 | B2 * | 1/2010 | Bae | B01F 11/0017 366/111 |
| 8,602,636 | B2 * | 12/2013 | Kauling | C12M 23/14 366/213 |
| 9,340,763 | B2 * | 5/2016 | Damren | C12M 41/24 |
| 2009/0152184 | A1 | 6/2009 | Liao et al. | |
| 2009/0180933 | A1 * | 7/2009 | Kauling | B01J 19/28 422/82.08 |
| 2010/0015696 | A1 | 1/2010 | Claes et al. | |
| 2010/0129899 | A1 | 5/2010 | Oosterhuis et al. | |
| 2011/0014689 | A1 * | 1/2011 | Gandlur | C12M 23/14 435/289.1 |
| 2015/0299641 | A1 * | 10/2015 | Galliher | C12M 41/24 435/298.1 |

FOREIGN PATENT DOCUMENTS

| | | |
|---|---|---|
| JP | 2-500081 A | 1/1990 |
| JP | 6-253815 A | 9/1994 |
| JP | 2007-534335 A | 11/2007 |
| JP | 2010-529854 A | 9/2010 |
| JP | 2014-121302 A | 7/2014 |
| WO | 2005/108546 A2 | 11/2005 |
| WO | 2007/134267 A2 | 11/2007 |

OTHER PUBLICATIONS

International Search Report received in corresponding International Application No. PCT/JP2016/069631 dated Sep. 6, 2016.
Chinese Office Action received in corresponding Chinese Application No. 201680045254.2 dated Apr. 1, 2021.
Chinese Office Action received in corresponding Chinese Application No. 201680045254.2 dated Jan. 7, 2021.
Baolin, H., Biological Engineering Equipment and Operation Technology, "Twelfth Five-Year" National Planning Textbook for Vocational Education, Sep. 2014, pp. 65-66.

* cited by examiner

SINGLE-USE CELL CULTURING APPARATUS AND CULTURING BAG

CROSS REFERENCE TO RELATED APPLICATION

This application is a National Stage Application of PCT/JP2016/069631, filed on Jul. 1, 2016, and which application is incorporated herein by reference. To the extent appropriate, a claim of priority is made to the above disclosed application.

TECHNICAL FIELD

The present invention relates to a single-use cell culturing apparatus and a culturing bag.

BACKGROUND ART

In producing biopharmaceuticals, a technique is used in which a living cell of a microorganism, an animal, a plant, a fungi, or the like is cultured. A conventional technique of culturing a living cell has been using a stainless culture tank. The living cell and a culture solution are put in the culture tank and are stirred therein by a stirring means.

When one culture is completed and another is to be started, the culture tank and the stirring means such as a stirrer are cleaned and sterilized, before a new culture solution is put in the culture tank. In this case, accompanying facilities including a steam supply apparatus for sterilizing inside the culture tank and a cleaning mechanism for cleansing are required and are not always easy to handle.

A single-use culture system has been recently known in which a living cell is cultured using a disposable flexible bag (that is, an only-once-used culture system). The single-use culture system typically includes: a flexible single-use culturing bag made of a plastic film or the like; and a support unit (a housing) that accommodates the culturing bag and keeps a shape thereof.

The culturing bag is sterilized by previously irradiating gamma rays, ultraviolet rays, or the like and is kept in a clean condition. This makes it possible to eliminate needs for processes of sterilization and cleansing, accompanying facilities, or the like, which are necessary in the above-described system using the stainless culture tank. Inventions related to the single-use culture system are disclosed in, for example, Japanese Laid-Open Patent Application, Publication No. 2014-121302 and Japanese Translation of PCT International Application Publication No. 2007-534335, which may also be referred to as Patent Documents 1 and 2, respectively.

More specifically, Patent Document 1 discloses a culture bag which contains a culture solution including an object to be cultured in order to culture the object to be cultured. The culture bag is provided with: a bag body formed of plastic material; a stirrer rotatably mounted in the bag body in order to stir the culture medium, and a baffle mounted in the bag body. The baffle is provided with a baffle opening which the object to be cultured can pass through.

Patent Document 1 also discloses that the baffle of the culture bag is integrally coupled by heat sealing with a film of which the culture bag is made. In another example, the baffle in the culture bag is supported by a baffle support unit provided outside the culture bag.

Patent Document 2 discloses a stirred-tank reactor system that includes: (i) a flexible bag with at least one opening, wherein the bag functions as a sterile container for a fluidic medium; (ii) a shaft situated within the bag; (iii) an impeller attachable to the shaft, wherein the impeller is used to agitate the fluidic medium to provide a hydrodynamic environment; and (iv) a bearing attached to the shaft and to the opening of the bag.

Patent Document 2 also discloses that the housing includes a plurality of baffles such that the bag is folded around the baffles.

RELATED ART DOCUMENTS

Patent Documents

Patent Document 1: Japanese Laid-Open Patent Application, Publication No. 2014-121302
Patent Document 2: Japanese Translation of PCT International Application Publication No. 2007-534335

SUMMARY OF THE INVENTION

Problem to be Solved by the Invention

The baffle disclosed in Patent Document 1 is provided such that flows in up and down directions in the culture solution are enhanced, and efficiency of stirring is improved.

One of the inventions in Patent Document 1 discloses that, when the baffle is coupled by heat sealing with the film of which the culture bag is made, upon pressure placed on a coupled portion, the coupled portion may be broken or peeled off due to hydrodynamic force applied to the baffle. There is thus a possibility of leakage of the culture solution. If and when a coupling temperature or a coupling time is not appropriate, to thereby make the coupling incomplete, then there is also a possibility of leakage of the culture solution. In another example disclosed in Patent Document 1, when pressure is placed on a part supported by the baffle support part, the culture bag may be broken, and there is also a possibility of leakage of the culture solution.

One of the inventions disclosed in Patent Document 2 discloses that the culture bag is folded around a plurality of the baffles provided in the housing. Thus, when pressure is placed onto a folded portion, there is a possibility that the culture bag is broken. Therefore, in the above-described invention disclosed in Patent Document 2, there is a possibility of leakage of the culture solution, similarly to the above-described invention disclosed in Patent Document 1.

In light of the described above, the present invention has been made in an attempt to provide a single-use cell culturing apparatus and a culturing bag which can improve efficiency of stirring a culture solution and can further reduce a possibility of leakage of the culture solution.

Means for Solving the Problem

A single-use cell culturing apparatus includes a housing that accommodates a culturing bag which is flexible and can seal a culture solution inside thereof. The housing has, on an inner surface thereof, a curved convex-shaped protrusion provided at a portion of a contact face at which the housing is in contact with the culturing bag.

A culturing bag is accommodated in a housing of a single-use cell culturing apparatus, is flexible, and is capable of sealing a culture solution inside thereof. The culturing bag has therein a concave portion having a shape corresponding to a curved convex protrusion disposed on a part of the housing.

Advantageous Effect of the Invention

The present invention can provide a single-use cell culturing apparatus and a culturing bag which can improve efficiency of stirring a culture solution and can further reduce a possibility of leakage of the culture solution.

BRIEF DESCRIPTION OF THE DRAWINGS

FIG. 2 is a cutaway view of a housing illustrating an example of a protrusion in

FIG. 1.

EMBODIMENTS FOR CARRYING OUT THE INVENTION

Next are described in detail a single-use cell culturing apparatus (which may also be referred to as a "cell culturing apparatus" hereinafter) and a culturing bag according to embodiments of the present invention with reference to related drawings.

The cell culturing apparatus and the culturing bag of the present invention are applicable to culturing of a cell of a microorganism, an animal, a plant, or the like, which produces a substance as a main raw material of a pharmaceutical product, a health food, or the like. In the present invention, such a substance to be produced is not, however, limited to the described above. Another substance to be produced includes, for example: protein such as an antibody and an enzyme; a physiologically active substance such as a low-molecular compound and a high-molecular compound; and a virus. Other substances to be produced include, for example: a carotenoid such as beta-carotene and astaxanthin; a pigment such as chlorophyll and bacterio-chlorophyll; phycobilin protein such as phycocyanin for use in coloring food, cosmetics, or the like; and a physiologically active substance such as fatty acid.

The cell to be cultured includes an animal cell, a plant cell, a photosynthetic bacterium, microalgae, blue algae, an insect cell, a bacterinum, a fermentum, a fungus, and algae. In particular, the cell to be cultured is preferably an animal cell which produces protein such as an antibody and an enzyme. A culture medium for use in culturing is not specifically limited, and any known culture medium can be used.

<An Embodiment of Cell Culturing Apparatus>

Figure 1:
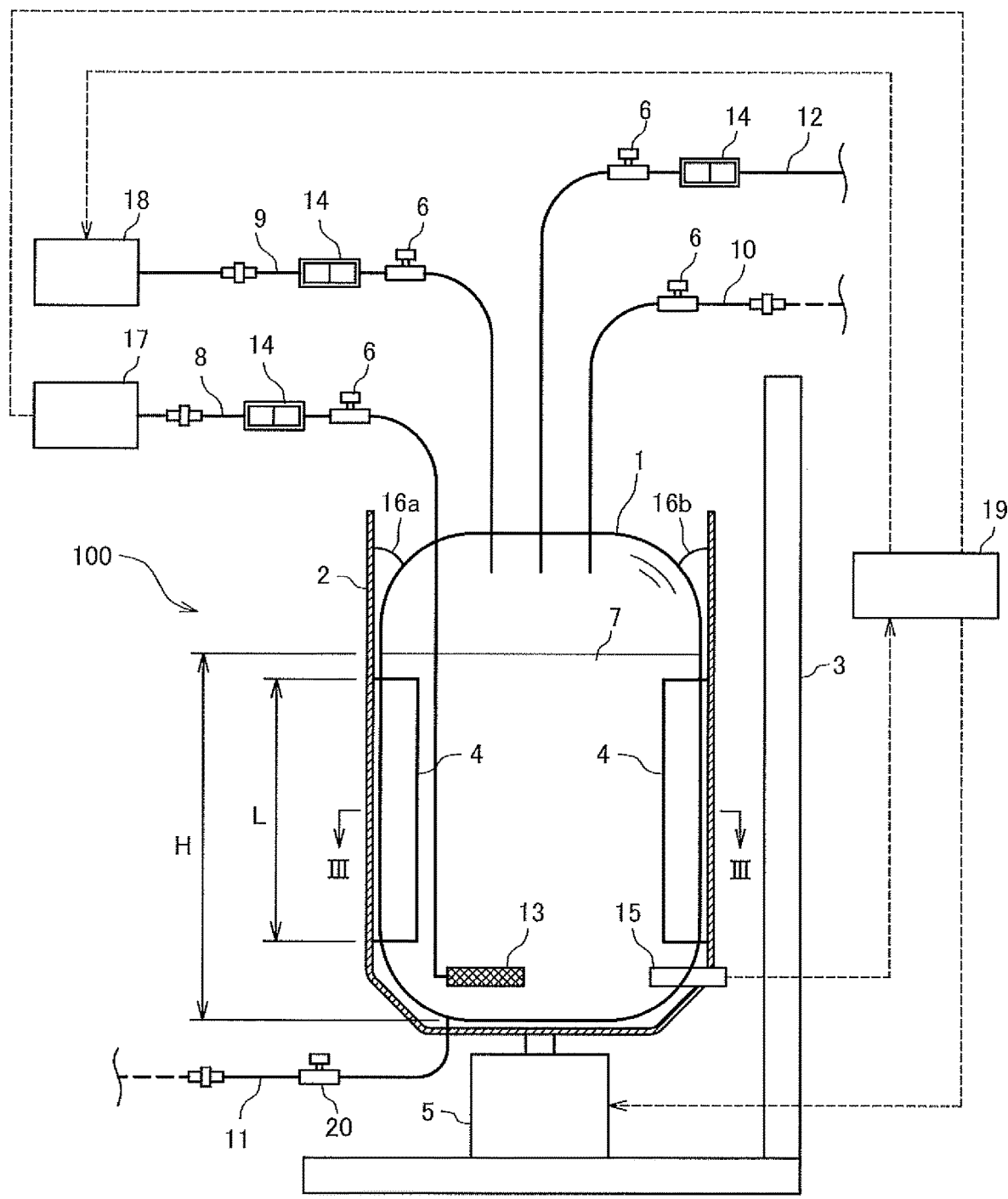
FIG. 1 is a schematic block diagram illustrating a single-use cell culturing apparatus according to an embodiment of the present invention.

FIG. 1 is a schematic block diagram illustrating a cell culturing apparatus according to an embodiment of the present invention.

As illustrated in FIG. 1, a cell culturing apparatus 100 includes a culturing bag 1 and a housing 2 in which the culturing bag 1 is accommodated. The housing 2 has two curved convex protrusions 4, 4, on respective portions of contact faces at which the housing 2 is in contact with the culturing bag 1. Note that FIG. 1 illustrates the housing 2 when the culturing bag 1 in which a culture solution 7 is sealed is accommodated. As illustrated in FIG. 1, the cell culturing apparatus 100 also includes a stirring unit which stirs the culture solution 7 contained in the culturing bag 1. As the stirring unit, more specifically, a stirring drive device 5 is installed below the housing 2 and is fixed to a support stand 3. The stirring drive device 5 stirs the culture solution 7 sealed in the culturing bag 1, by rotating the housing 2 in a position eccentric from the center axis thereof.

Though not illustrated in FIG. 1, the cell culturing apparatus 100 has: a gas supply equipment such as air, oxygen, nitrogen, and carbon dioxide; hot and cold water supply equipment; and feed-water and drainage equipment, all of which are indispensable for culturing. The cell culturing apparatus 100 also has: a culture medium in which an appropriate composition for culturing a target cell is prepared in advance, equipment for supply a supplemented medium which is added in a feeding culture during culturing, or the like.

<Housing and Support Stand>

Each of the housing 2 and the support stand 3 of any type can be used as long as the each of the housing 2 and the support stand 3 has enough strength to support weight or pressure of the culturing bag 1 into which the culture solution 7 is put, and to maintain a shape thereof. Any material of which the each of the housing 2 and the support stand 3 is made is available such as metal and hard plastic.

<Protrusion>

Figure 2:
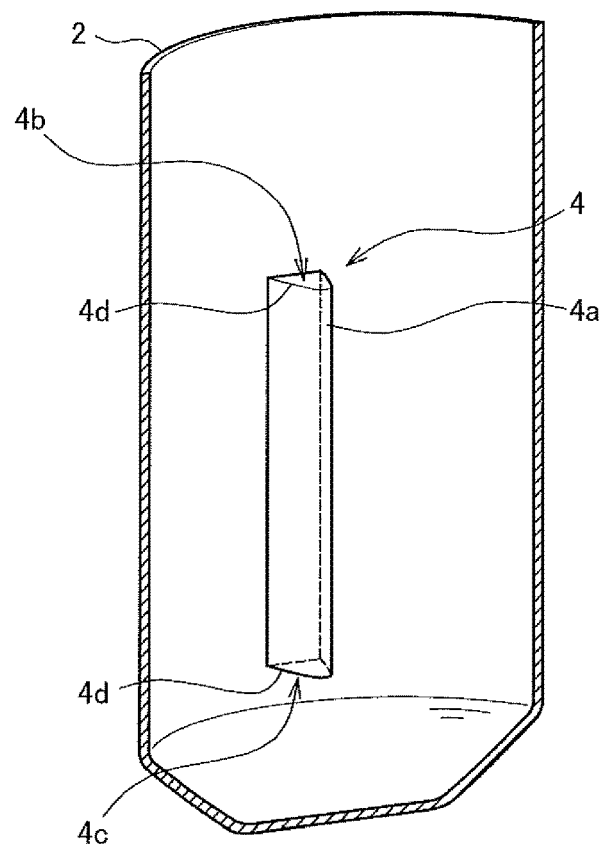
Figure 3:
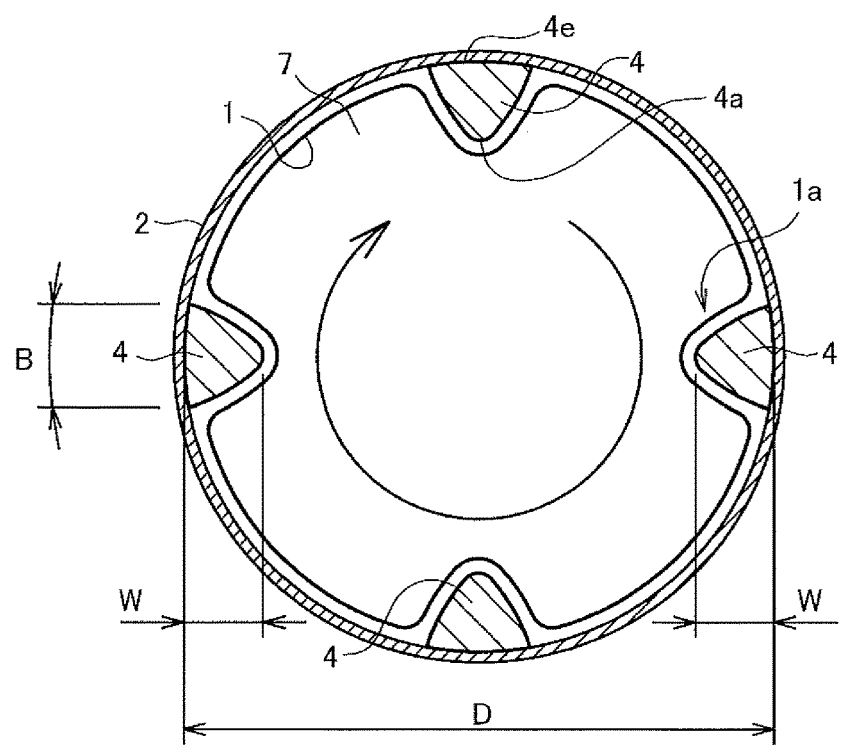
FIG. 3 a cross sectional view illustrating the single-use cell culturing apparatus when cut along the line III-Ill in FIG. 1.
Figure 4A:
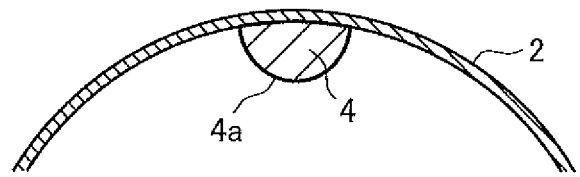
FIG. 4A is a cross sectional view illustrating another example of the protrusion.
Figure 4B:
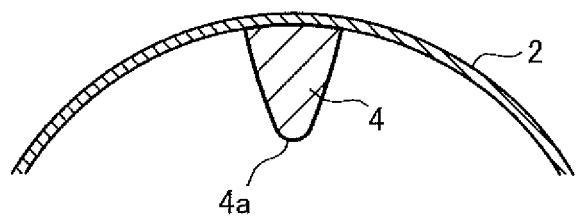
FIG. 4B is a cross sectional view illustrating a still another example of the protrusion.
Figure 4C:
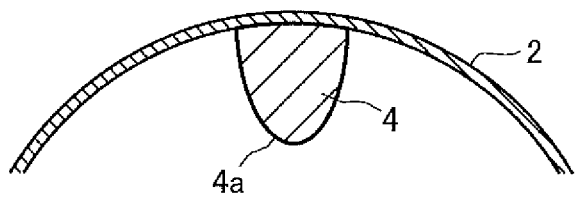
FIG. 4C is a cross sectional view illustrating a yet another example of the protrusion.

FIG. 2 is a cutaway view of the housing 2 illustrating an example of the protrusion 4 illustrated in FIG. 1. FIG. 3 is a cross sectional view of the cell culturing apparatus when cut along the line III-III in FIG. 1. For convenience of explanation and illustration, the culturing bag 1 in FIG. 3 is illustrated in such a state that the culturing bag 1 is spaced above and apart from an inner wall of the housing 2. In reality, however, pressure of the sealed culture solution 7 firmly presses the culturing bag 1 against the inner wall of the housing 2 or the protrusion 4. FIG. 4A to FIG. 4C are each a cross sectional view illustrating another example of the protrusion 4.

As illustrated in FIG. 2 and FIG. 3, the protrusion 4 has a substantially triangular prismatic shape. The shape is not, however, limited to this, and may be: substantially semicircular columnar as illustrated in FIG. 4A; substantially triangular prismatic with two triangular prismatic and slightly swollen surfaces which are to be brought in contact with the culturing bag 1, as illustrated in FIG. 4B; or substantially semi-ellipsoidal as illustrated in FIG. 4C. That is, the protrusion 4 of the present invention is formed such that a side 4a thereof is slightly rounded (curved) so as to prevent the culturing bag 1 from being broken when pressure is applied thereto. Because the cell culturing apparatus 100 has the protrusion 4 described above, the culture solution 7 while being stirred hits against the protrusion 4, which can enhance flows in the up and down directions. The cell culturing apparatus 100 can thus improve efficiency of stirring the culture solution 7. Note that both an upper end 4b and a lower end 4c of the protrusion 4 illustrated in FIG. 2 can be made open. The open ends 4b, 4c may be, however, made closed by covering with a plate, a cap, or any other appropriate material (The same applies to examples illustrated in FIG. 5, FIG. 6, and FIG. 7). Sides 4d, 4d, which form the upper end 4b and the lower end 4c are preferably machined to be rounded out. This allows the culturing bag 1 to be more tear-proof.

As illustrated in FIG. 2 and FIG. 3, roundness of the side 4a is preferably, for example, 0.05 to 0.5 times a length of a base 4e in terms of a radius of curvature. When the radius of curvature of the side 4a is kept within the range, the culturing bag 1 can be made more proof against breakage, because the side 4a has appropriate roundness. For purpose of further preventing the culturing bag 1 from being broken, the radius of curvature of the side 4a is preferably not less than 0.2 and not more than 0.45.

As illustrated in FIG. 3, a height W of the protrusion 4 preferably has a W/D within a range from 0.05 to 0.15, wherein D is an internal dimension of the housing 2. When the height W and the internal dimension D of the protrusion 4 have the above relationship, up and down flows of the culture solution 7 can be further enhanced without excessively blocking swirling flow of the culture solution 7 while being stirred. This makes it possible for the cell culturing apparatus 100 to further improve stirring efficiency. For purpose of further improving stirring efficiency, the height W of the protrusion 4 is preferably not less than 0.08 and is also preferably not more than 0.13 of the W/D.

The height W of the protrusion 4 may be, as illustrated in FIG. 3, made 0.5 to 5 times a length B of a base on a cross sectional surface of the protrusion 4. Similarly to the above, when the height W and the length B of the base of the protrusion 4 have the above relationship, up and down flows of the culture solution 7 can be further enhanced without excessively blocking swirling flow of the culture solution 7 while being stirred. This makes it possible for the cell culturing apparatus 100 to further improve stirring efficiency. For purpose of further improving stirring efficiency, the height W of the protrusion 4 is preferably not less than a submultiple of the length B of the base of the protrusion 4 and is also preferably not more than 3 of the W/D.

Figure 5:
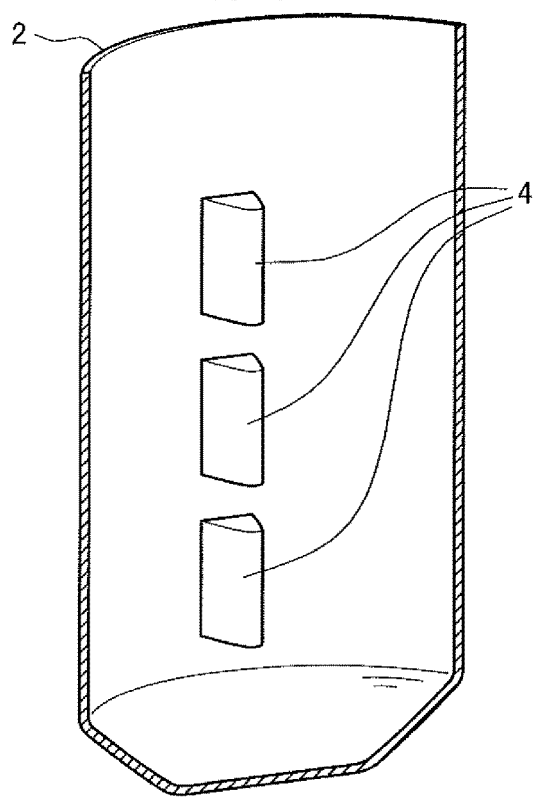
FIG. 5 is a cutaway view of the housing illustrating another example of the protrusion.

A length L in a longitudinal direction of the protrusion 4 is, as illustrated in FIG. 1, preferably within a range from not less than 0.05 to not more than 1 in terms of a L/H, wherein H is a liquid level height of the culture solution 7 sealed in the culturing bag 1. As illustrated in FIG. 5, the protrusion 4 may be divided into a plurality and then arranged on a same line. In this case, the length L is assumed to be a total of lengths of the protrusions 4, 4, 4 each having been divided and arranged on the same line (In this example, a distance between one protrusion 4 and another 4 is not included in the length L). Note that FIG. 5 is a cutaway view of the housing 2 illustrating another example of the protrusion 4.

When the relationship between the length L of the protrusion 4 in the longitudinal direction and the liquid level height H of the culture solution 7 takes a value within the range described above, similarly to the aforementioned, up and down flows of the culture solution 7 can be further enhanced without excessively blocking swirling flow of the culture solution 7 while being stirred. This makes it possible for the cell culturing apparatus 100 to further improve stirring efficiency. For purpose of further improving stirring efficiency, the length L in the longitudinal direction of the protrusion 4 is preferably not less than 0.3 and is also preferably not more than 0.8 in terms of the L/H.

Figure 6:
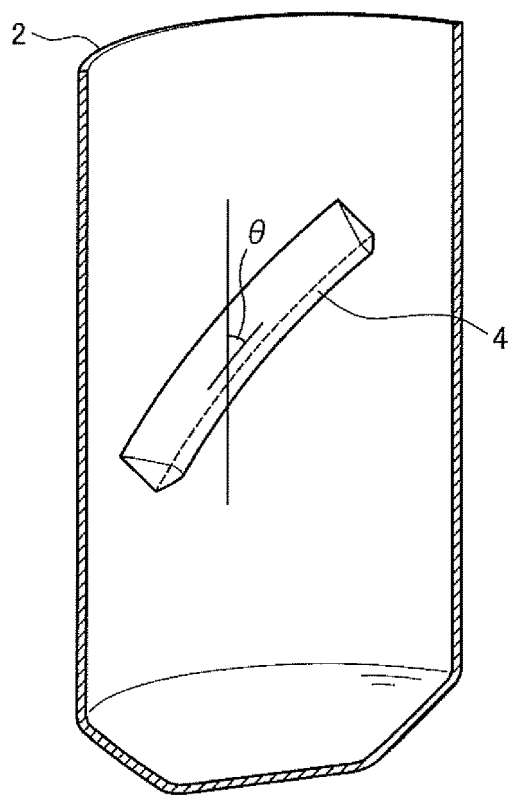
FIG. 6 is a cutaway view of the housing illustrating a still another example of the protrusion.

The protrusion 4 described above is provided, as illustrated in FIG. 1 to FIG. 3, on a sidewall of the housing 2 in a direction parallel to a vertical direction. The protrusion 4 may also be provided, as illustrated in FIG. 6, on the sidewall of the housing 2 at a prescribed tilt angle θ with respect to the vertical direction. FIG. 6 is a cutaway view of the housing 2 illustrating a still another example of the protrusion 4.

The prescribed tilt angle θ can be freely selected. When the vertical direction is assumed to take, for example, 0 degrees the prescribed angle θ is preferably more than 0 degrees and not more than 45 degrees. Similarly to the aforementioned, even when the protrusion 4 is tilted as described above, up and down flows of the culture solution 7 can be enhanced.

Figure 7:
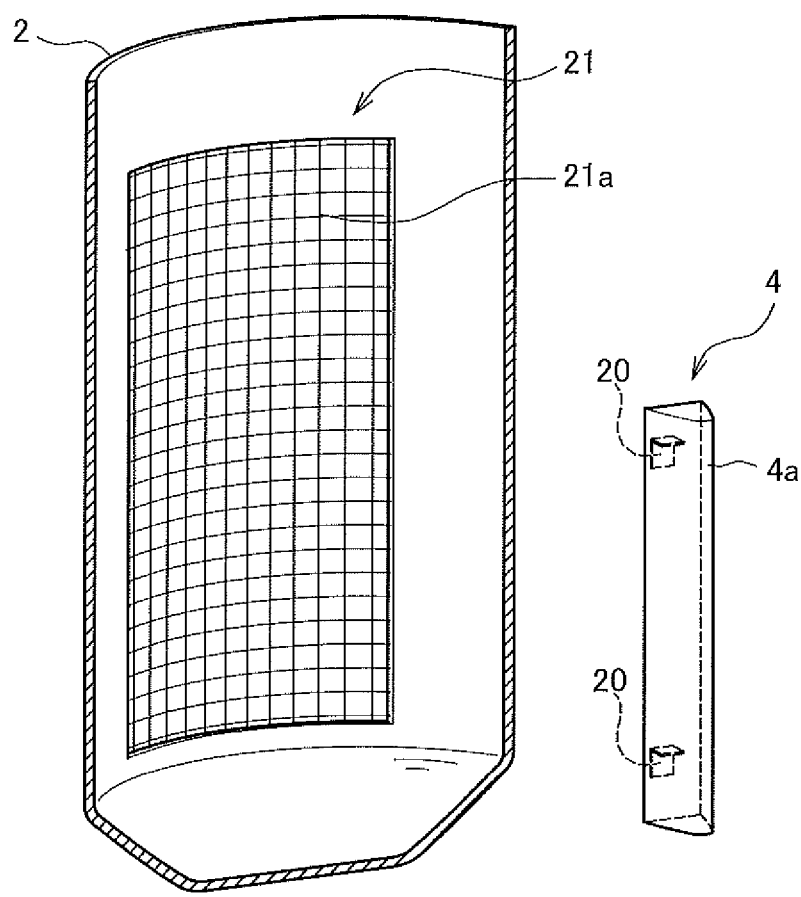
FIG. 7 is a cutaway view of the housing illustrating a yet another example of the protrusion.

The protrusion 4 can be mounted detachably. FIG. 7 is a cutaway view illustrating a yet another example of the housing 2 and the protrusion 4.

As illustrated in FIG. 7, a fixing mechanism 21 having one or more holes 21a in the housing 2 is provided as the yet another example. The protrusion 4 has a fixing part 20 with which the protrusion 4 is fixed to the hole 21a of the fixing mechanism 21.

The fixing mechanism 21 may be of any type, as long as the fixing mechanism 21 can fix the protrusion 4 using the fixing part 20. The fixing mechanism 21 is formed by, for example, punching metal or wire net. The fixing part 20 is preferably formed on a face-to-face side of the side 4a, that is, on the base side of the protrusion 4. This makes it possible to prevent the culturing bag 1 from being broken which would otherwise occur due to a possible contact of the fixing part 20 with the culturing bag 1. The fixing part 20 may be, for example, a convex member in such a shape that fits in with a punching metal hole, a hook which catches onto a mesh of a wire net, or the like.

With the fixing mechanism 21 and the fixing part 20, a position and an angle of mounting the protrusion 4 can be freely changed and the protrusion 4 can be detachably fixed.

(Culturing Bag)

The culturing bag 1 used in the present invention can be, as illustrated in FIG. 1, of any type without specific limitations, as long as the culturing bag 1: can be accommodated in the housing 2 of the cell culturing apparatus 100; is flexible; and can seal the culture solution 7 inside thereof.

The culturing bag 1 suitably used herein is prepared by using a multi-layered film made of, for example, ethylene vinyl acetate, ethyl vinyl alcohol, or the like. As the culturing bag 1 described above, any of single-use bags for use in medicinal product packaging which are commercially available by various manufacturers can be freely selected and used. Note that those culturing bags available in the market are typically kept sterile in folded states with substantially no contents left therein such as gas and liquid, after being sterilized by gamma rays, ultraviolet rays, ethylene oxide gas, or the like.

When the culturing bag 1 as described above is used, the housing 2 preferably has a concave portion 1a (see FIG. 3) which is provided in a shape corresponding to the curved convex protrusion 4. This makes it possible for the protrusion 4 of the housing 2 and the concave portion 1a of the culturing bag 1 to fit into each other, when the culturing bag 1 is set in the housing 2. This allows the culturing bag 1 to be less likely to subject to load. That is, because excessive pressure is not unnecessarily applied to the culturing bag 1, the culturing bag 1 can be further prevented from being broken.

The culturing bag 1 is connected to a gas supply pipe for in-liquid aeration 8, a gas supply pipe for gas phase 9, a culture medium feed pipe 10, a culture solution exhaust pipe 11, and a gas exhaust pipe 12.

The gas supply pipe for in-liquid aeration 8 includes a tip end disposed inside the culturing bag 1 which is connected to an air diffusion unit 13 for generating air bubbles. The air diffusion unit 13 is disposed on a bottom along the sidewall of the culturing bag 1, by means of fusion or the like. With the air diffusion unit 13 provided as described above, the air bubbles generated by the air diffusion unit 13 produce an upward flow in the culture solution 7. Thus, efficiency of stirring the culture solution 7 can be further improved.

A valve 6 is disposed in each of the gas supply pipe for in-liquid aeration 8, the gas supply pipe for gas phase 9, the culture medium feed pipe 10, the culture solution exhaust pipe 11, and the gas exhaust pipe 12 and appropriately controls ON/OFF of aeration and liquid passage or a flow rate thereof.

A gas filter 14 is disposed in each of the gas supply pipe for in-liquid aeration 8, the gas supply pipe for gas phase 9, and the gas exhaust pipe 12, so as to prevent invasion of microorganisms from outside. Note that other pipes for sampling, injecting a pH regulator, exchanging a medium, or the like can be provided, description of which is omitted in FIG. 1, though.

A measurement unit 15 is also provided for measuring a culture state, which actually includes: a device for measuring a pH, a temperature, a dissolved oxygen level, a dissolved carbon dioxide level, or the like; and a sensor thereof. The measurement unit 15 is illustrated in FIG. 1 in a simplified manner.

(Operation Method)

An operation method (a procedure of culturing operations) of the cell culturing apparatus 100 and the culturing bag 1 described above is explained below in detail with reference to FIG. 1. Note that the following explanation is focused on outline of the operation. It is to be understood that the present invention is not necessarily limited to the following procedure.

The culturing bag 1 is provided in a folded state and is appropriately set up by being positioned such that the culturing bag 1 is situated at a prescribed mounting position in the housing 2, using position fixing support members 16a, 16b. In setting up, if the housing 2 has an opening at an upper part thereof, the culturing bag 1 can be inserted from the upper opening and is appropriately arranged. If the housing 2 has an opening at a sidewall, the culturing bag 1 can be inserted from the sidewall opening and is appropriately arranged. In this case where the housing 2 has the opening on the sidewall thereof, it is preferable to use a publicly known opening/closing mechanism.

The culturing bag 1 is filled via the culture medium feed pipe 10 with the culture solution 7 in which a target cell and a medium are suspended. The culturing bag 1 is filled with the culture solution 7 after the culture solution 7 is prepared to have a predetermined cell concentration. Alternatively, the culturing bag 1 is filled with a culture medium, after which a cell is inoculated thereon such that the culture solution 7 is prepared to have the predetermined cell concentration. It is to be understood that a culture medium feed tank or a culture solution preparation tank, both not illustrated, are sterilely connected to the culture medium feed pipe 10. In any of those cases, pressure from gravity of the filled culture solution 7 firmly presses the culturing bag 1 against the inner wall of the housing 2 and the protrusion 4.

As a result of the described above, a baffle is thus formed by the curved convex protrusion 4 on an inner wall of the culturing bag 1 which is in contact with the housing 2.

As described above, the stirring drive device 5 is installed on the support stand 3. The stirring drive device 5 stirs the culture solution 7 by means of shake culture in which the culturing bag 1 and the housing 2 are integrally rotated in a position eccentric from the center axis thereof. When the stirring drive device 5 is operated, the culture solution 7 in the culturing bag 1 is made to flow and is stirred up. As illustrated in FIG. 3, when the stirring drive device 5 is in operation, swirling flow in a horizontal direction is typically generated in the culture solution 7. However, part of the culture solution 7 at an outer periphery hits the baffle formed by the protrusion 4 (in FIG. 3, four units of the protrusions 4 are exemplified). A direction of part of the swirling flow is thus changed, to thereby generate flows in the up and down directions. This makes it possible to efficiently stir the culture solution 7 so as to obtain uniformity thereof.

The culturing bag 1 is connected to the gas supply unit for in-liquid aeration 17 via the gas supply pipe for in-liquid aeration 8 and the gas supply unit for gas phase 18 via the gas supply pipe for gas phase 9, respectively. The gas supply unit for in-liquid aeration 17 and the gas supply unit for gas phase 18 are operated. Oxygen mixture gas at a prescribed concentration is aerated in the culturing bag 1. Culturing is thus started.

Oxygen gas aerated in or on the culture solution 7 dissolves therein. As described above, the direction of the swirling flow is turned, to thereby generate flows in the up and down directions and then produce an overall flow in the culturing bag 1. This makes it possible to uniformly supply oxygen to the cell in the culture solution 7 during culturing and also to improve efficiency of stirring the culture solution 7.

The measurement device and the sensor which are collectively described as the measurement unit 15 measures a pH, a temperature, a DO (dissolved oxygen level), and a $DCO_2$ (dissolved carbon dioxide level), and inputs the measured result into a control device 19. The control device 19 adjusts an amount of aeration of each of air, oxygen, and nitrogen contained in a mixed gas, to thereby maintain a prescribed pH, DO, and $DCO_2$ and continue the culturing. The culture solution exhaust pipe 11 or a sampling tube (not illustrated) can measure a cell concentration and a medium component concentration, after sterilely taking out part of the culture solution 7 during culturing. When the cell concentration is measured using optical turbidity, a turbidity sensor is provided as the measurement unit 15 described above. This makes it possible to, during culturing, maintain a culture environment in the culture solution 7 in a condition appropriate for culturing a target cell.

When the culturing is completed, the stirring drive device 5 is stopped, and shaking of the housing 2 is thereby stopped. The culture solution 7 is then exhausted via the culture solution exhaust pipe 11 disposed at a lower part of the culturing bag 1. A post process such as collection and purification of a target culture product from the exhausted culture solution 7 is then performed, at which a set of culture production steps is completed.

After the culture solution 7 is exhausted, the culturing bag 1 is removed from the housing 2 and is discarded. When another set of culture production steps is started, another culturing bag 1 is set in the housing 2.

(Another Embodiment of Cell Culturing Apparatus)

Figure 8:
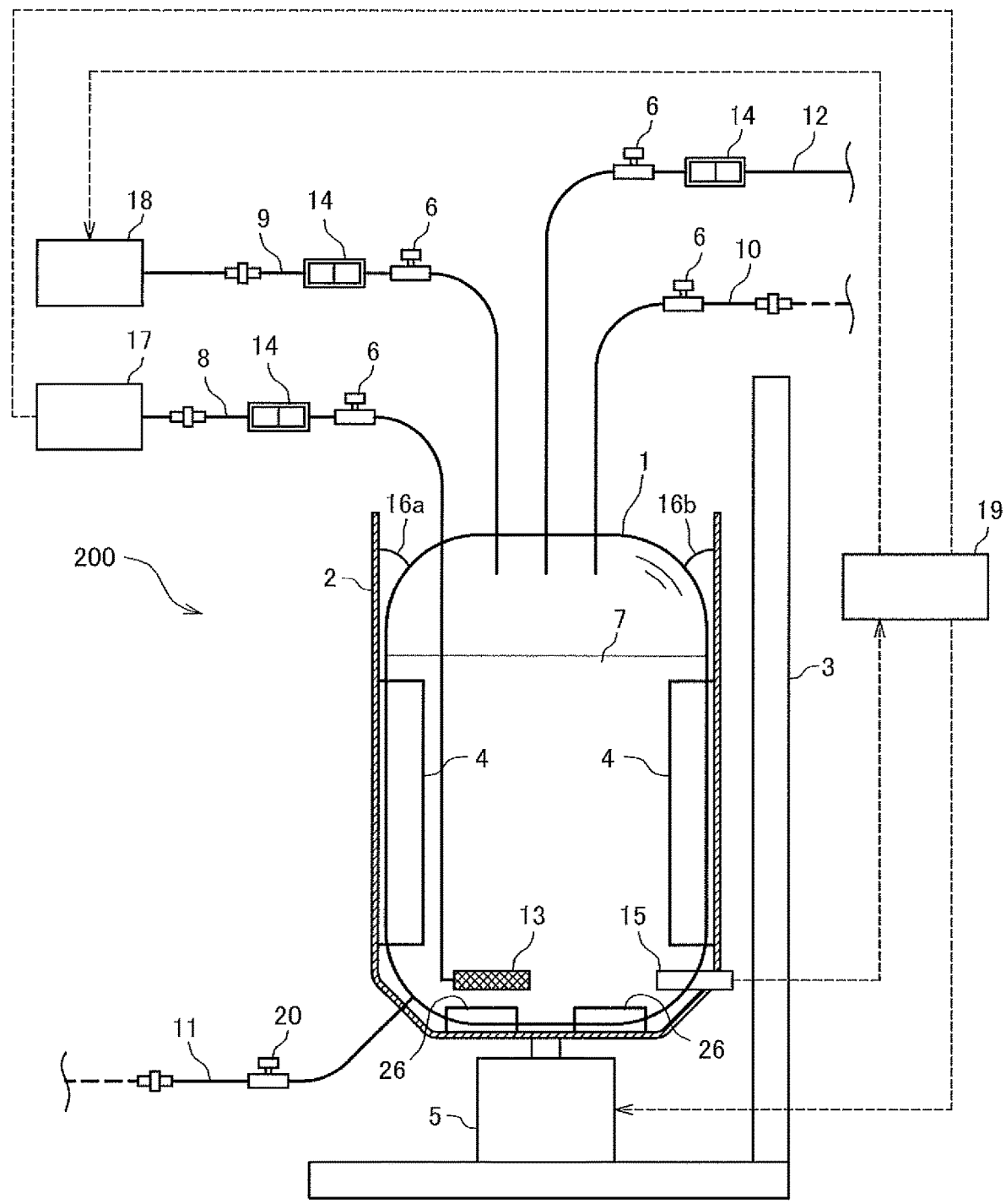
FIG. 8 is a schematic block diagram illustrating a single-use cell culturing apparatus according to another embodiment of the present invention.

FIG. 8 is a schematic block diagram illustrating a cell culturing apparatus according to another embodiment of the present invention. A cell culturing apparatus 200 illustrated in FIG. 8 has a structure same as that of the cell culturing apparatus 100 described above, except that the cell culturing apparatus 200 includes a curved convex protrusion 26 disposed at a bottom of the housing 2. Description of the cell culturing apparatus 200 is thus made focusing on a structure different from the cell culturing apparatus 100, and description of a structure similar to the cell culturing apparatus 100 is omitted herefrom.

Figure 9A:
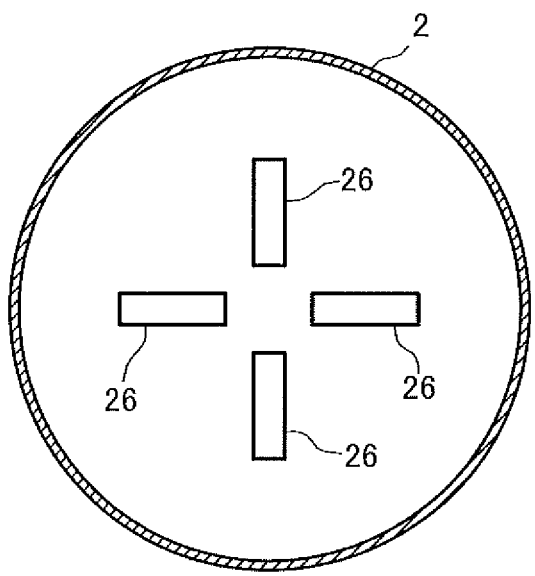
FIG. 9A is a schematic diagram illustrating an example of the protrusion disposed on a bottom of the housing.

FIG. 9A is a schematic diagram illustrating an example of the protrusion 26 disposed on the bottom of the housing 2. As illustrated in FIG. 9A, four protrusions 26 are radially arranged from a center position of the bottom of the housing 2 at equal intervals.

Figure 9B:
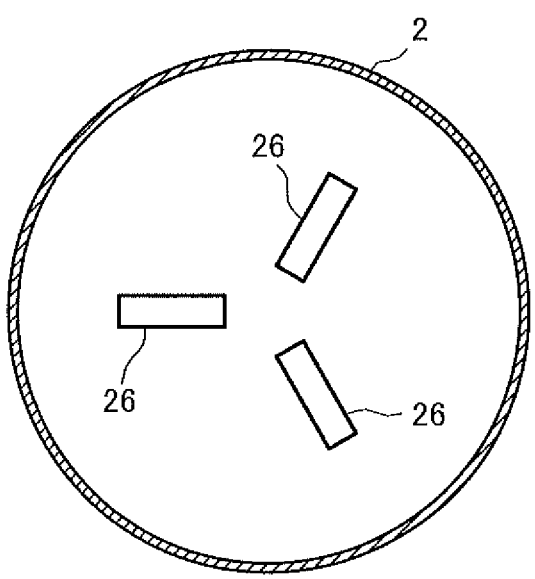
FIG. 9B is a schematic diagram illustrating another example of the protrusion disposed on the bottom of the housing.

FIG. 9B is a schematic diagram illustrating another example of the protrusion 26 disposed on the bottom of the housing 2. As illustrated in FIG. 9B, three protrusions 26 are radially arranged from the center position of the bottom of the housing 2 at equal intervals.

When the protrusion 26 is disposed in the examples illustrated in each of FIG. 9A and FIG. 9B, in any of these cases, the culture solution 7 during being stirred hits the protrusion 26, and flows in the up and down directions are thus made stronger. The cell culturing apparatus 200 can further improve efficiency of stirring the culture solution 7.

Figure 10A:
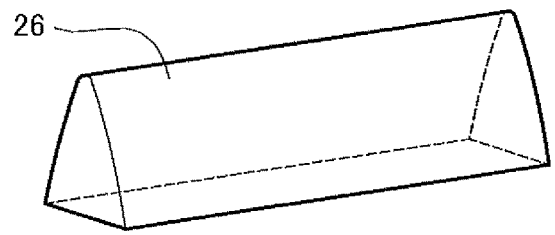
FIG. 10A is a perspective diagram illustrating a specific shape of the protrusion.

FIG. 10A is a perspective diagram illustrating a specific shape of the protrusion 26. FIG. 10B to FIG. 10E are each a cross sectional view illustrating another specific shape of the protrusion 26.

Figure 10B:
FIG. 10B is a perspective diagram illustrating another specific shape of the protrusion.

The protrusion 26 has, as illustrated in FIG. 10A or FIG. 10B, a substantially triangular prismatic shape. Note that the protrusion 26 illustrated in FIG. 10A is different from the protrusion 26 illustrated in FIG. 10B in that the protrusion 26 illustrated in FIG. 10B has a larger radius of curvature of a side 26a than that illustrated in FIG. 10A.

Figure 10C:
FIG. 10C is a perspective diagram illustrating a still another specific shape of the protrusion.
Figure 10D:
FIG. 10D is a perspective diagram illustrating a yet another specific shape of the protrusion.
Figure 10E:
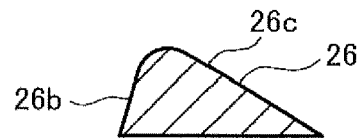
FIG. 10E is a perspective diagram illustrating a further specific shape of the protrusion.

The protrusion 26 may have: as illustrated in FIG. 10C, a substantially semicircular columnar shape; and, as illustrated in FIG. 10D, a substantially semi-ellipsoidal shape. The protrusion 26 may have, as illustrated in FIG. 10E, an asymmetric shape in which an area of a face 26c is different from that of another face 26c.

(Still Another Embodiment of Cell Culturing Apparatus)

Description above is made by way of example, in which each of the cell culturing apparatus 100 and the cell culturing apparatus 200 includes the stirring drive device 5 which stirs the culture solution 7 by means of shake culture in which the culturing bag 1 and the housing 2 are integrally rotated in a position eccentric from the center axis thereof. How to stir the culture solution 7 of the present invention is not, however, limited to this, and various other techniques can be used.

Figure 11:
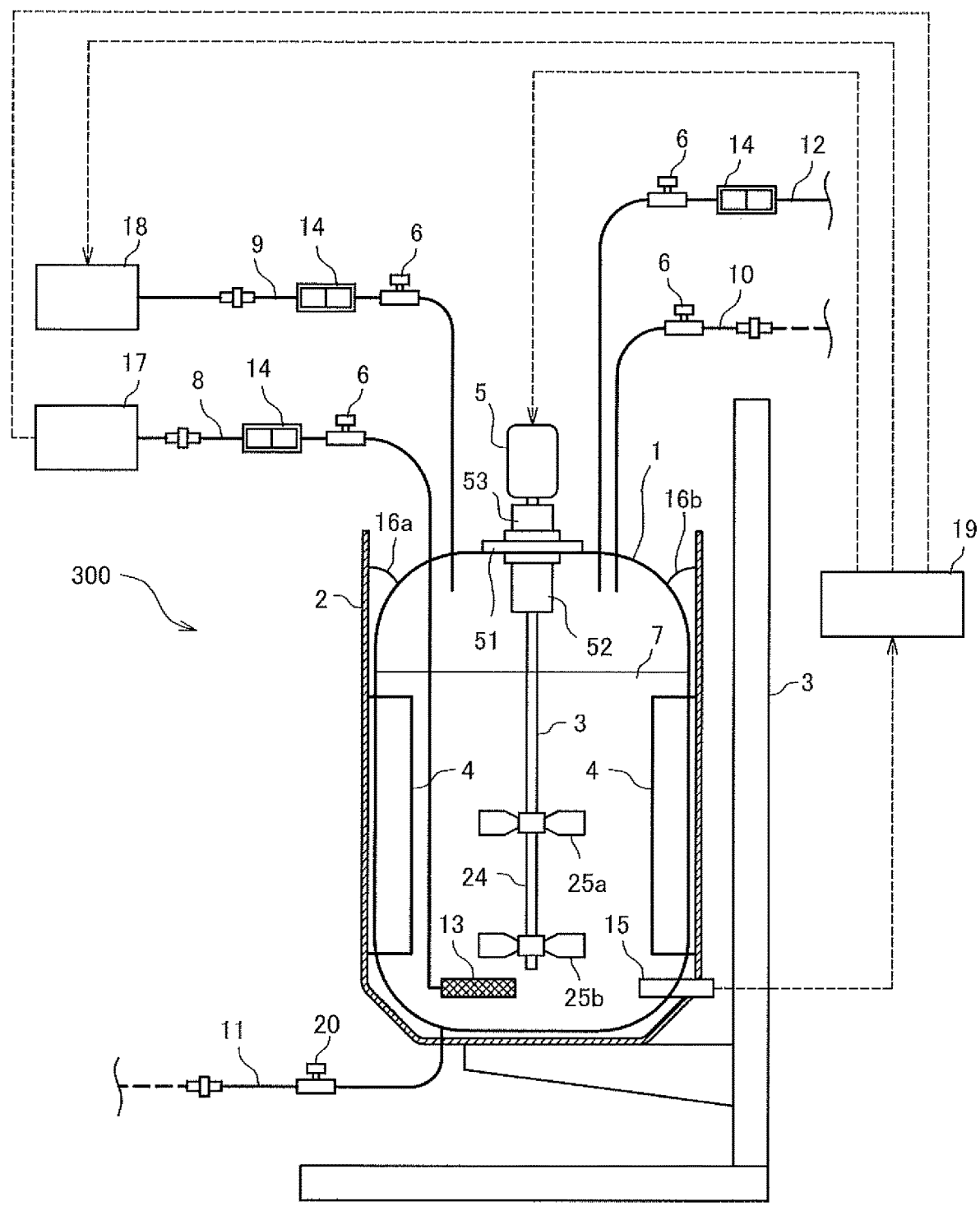
FIG. 11 is a schematic block diagram illustrating a single-use cell culturing apparatus according to a still another embodiment of the present invention.

FIG. 11 is a schematic block diagram illustrating a cell culturing apparatus according to a still another embodiment of the present invention.

A cell culturing apparatus 300 illustrated in FIG. 11 includes a magnetic coupling as the stirring drive device 5. The cell culturing apparatus 300 includes a top board 51 which is disposed on top of the culturing bag 1 accommodated in the housing 2. A magnetic coupling member 52 is disposed inside the culturing bag 1, which forms magnetic coupling with another magnetic coupling member 53 on the top board 51. The magnetic coupling member 52 is connected to a rotary shaft 24 having rigidity, and is immersed in the culture solution 7. A stirring blade 25a and a stirring blade 25b are fixed to the rotary shaft 24.

When the stirring drive device 5 is activated in response to an appropriate signal from the control device 19, the magnetic coupling member 53 starts rotating. The rotating force is transmitted to the rotary shaft 24 via the magnetic coupling member 52, which rotates the stirring blade 25a and the stirring blade 25b. The cell culturing apparatus 300 allows the culture solution 7 to be stirred without creating a through hole in the culturing bag 1. Note that a sealing mechanism for the stirring is not limited to the above-described technique using a magnetic coupling, and a publicly-known mechanical seal (a shaft seal device) can also be used. The procedure of culturing operation using the cell culturing apparatus 300 as illustrated in FIG. 11 is same as that using the cell culturing apparatus 100, except that different units for creating flows and stirring the culture solution 7 are used. The overlapped description thereof is thus omitted herefrom.

With the cell culturing apparatus and the culturing bag of the present invention as described above, efficiency of stirring the culture solution can be improved, because the housing has the curved convex protrusion. The curved convex protrusions does not require a joint or a support member, an operation of folding, or the like, which makes the culturing bag, even under pressure, free from being broken from causes related to the described above. A possibility of leakage of the culture solution can be thus further reduced.

In the present invention, efficiency of stirring the culture solution is improved. This enhances mixing of a cultured cell and a culture medium, and supply of dissolved oxygen needed for breathing of the cultured cell, thus allowing efficiency of culture production to be increased.

Improvement in efficiency of stirring the culture solution can reduce power required for performing cell culturing than that according to conventional technology, and also reduce cost of the power.

DESCRIPTION OF REFERENCE NUMERALS 100, 200, 300 cell culturing apparatus (single-use cell culturing apparatus)
1 culturing bag
1a concave portion
2 housing
4, 26 protrusion

The invention claimed is:
1. A single-use cell culturing apparatus, comprising:
a housing that has a cylindrical space with a center axis which is fixed in a vertical direction and configured to accommodate a cylindrical culturing bag which is flexible and can seal a culture solution inside thereof, the housing rotatable in a horizontal plane around an axis that is in an eccentric position from the center axis of the housing to stir the culture solution inside the bag by centrifugal force of rotation of the housing; and a curved convex-shaped protrusion provided on an inner sidewall surface of the housing at a position at which the housing comes in contact with the culturing bag and which corresponds to a location below a liquid level of the culture solution in the culturing bag.

2. The single-use cell culturing apparatus according to claim 1, wherein the culturing bag is accommodated in the housing.

3. The single-use cell culturing apparatus according to claim 1, wherein a W/D is within a range from 0.05 to 0.15, in which W is a height of the protrusion and D is an internal dimension of the housing.

4. The single-use cell culturing apparatus according to claim 1, wherein the protrusion is provided on the inner sidewall surface of the housing in a direction parallel to the vertical direction or at a prescribed tilt angle with respect to the vertical direction.

5. The single-use cell culturing apparatus according to claim 1, further comprising:

another protrusion disposed on an inner bottom surface of the housing.

6. The single-use cell culturing apparatus according to claim 1, wherein the inner sidewall surface of the housing has a plurality of holes, and wherein the protrusion includes a fixing part which is mountable in a plurality of positions and a plurality of angles to the holes of the inner sidewall surface of the housing and detachable therefrom.

7. The single-use cell culturing apparatus according to claim 1, wherein the protrusion has a substantially triangular prismatic shape or a substantially semicircular columnar shape.

8. The single-use cell culturing apparatus according to claim 1, wherein a height of the protrusion is 0.5 to 5 times a length of a base of the protrusion.

9. The single-use cell culturing apparatus according to claim 1, wherein a side of the protrusion is 0.05 to 0.5 times a length of a base in terms of a radius of curvature.

10. The single-use cell culturing apparatus according to claim 1, wherein a length L in a longitudinal direction of the protrusion is within a range from not less than 0.05 to not more than 1 in terms of a L/H, in which H is the liquid level height of the culture solution sealed in the culturing bag.

11. The single-use cell culturing apparatus according to claim 1, further comprising:

a support stand which supports the housing, wherein the housing is rotatable in the horizontal plane relative to the support stand.

* * * * *